United States Patent
Bastide et al.

(10) Patent No.: US 9,993,385 B2
(45) Date of Patent: Jun. 12, 2018

(54) VISUAL HEALTH MAINTENANCE AND IMPROVEMENT

(71) Applicant: International Business Machines Corporation, Armonk, NY (US)

(72) Inventors: Paul Bastide, Boxford, MA (US); Stefan von Cavallar, Melbourne (AU); Isabell Kiral-Kornek, Collingwood (AU); Fang Lu, Billerica, MA (US); Dwarikanath Mahapatra, Melbourne (AU); Susmita Saha, Melbourne (AU); Arun Vishwanath, Melbourne (AU)

(73) Assignee: International Business Machines Corporation, Armonk, NY (US)

( * ) Notice: Subject to any disclaimer, the term of this patent is extended or adjusted under 35 U.S.C. 154(b) by 0 days. days.

(21) Appl. No.: 15/271,694

(22) Filed: Sep. 21, 2016

(65) Prior Publication Data
US 2018/0078445 A1    Mar. 22, 2018

(51) Int. Cl.
*A61B 3/00* (2006.01)
*A61H 5/00* (2006.01)
*G08B 21/24* (2006.01)
*G06F 19/00* (2018.01)

(52) U.S. Cl.
CPC ........... *A61H 5/00* (2013.01); *G06F 19/3431* (2013.01); *G08B 21/24* (2013.01)

(58) Field of Classification Search
CPC ..... A61B 3/113; A61B 3/0091; A61B 5/1114; A61B 5/162; A61B 5/4064; A61B 5/4088
USPC ........................................ 351/203, 209, 210
See application file for complete search history.

(56) References Cited

U.S. PATENT DOCUMENTS

| | | | |
|---|---|---|---|
| 6,042,231 A | 3/2000 | Fateh | |
| 6,139,149 A | 10/2000 | Shafer et al. | |
| 6,592,223 B1 | 7/2003 | Stern et al. | |
| 8,000,535 B2 | 8/2011 | Speigle | |
| 8,340,274 B2 | 12/2012 | Saushkin | |
| 2016/0193104 A1* | 7/2016 | Du | G02C 7/081 351/203 |

FOREIGN PATENT DOCUMENTS

CN    2905044 Y    5/2007

OTHER PUBLICATIONS

G. Heiting et al., "Computer Eye Strain: 10 Steps for Relief," http://www.allaboutvision.com/cvs/irritated.htm, Jun. 20, 2016, 7 pages.
Michael Drake, "Improve Your Eyesight Naturally with Eye Exercises," http://www.motherearthnews.com/natural-health/improve-your-eyesight-naturally-zmaz83jazshe.aspx, Jul./Aug. 1983, 9 pages.

(Continued)

*Primary Examiner* — Mahidere Sahle
(74) *Attorney, Agent, or Firm* — Louis J. Percello; Ryan, Mason & Lewis, LLP

(57) ABSTRACT

A system to monitor visual health includes a processor operatively coupled to memory. The system further includes one or more subsystems configured to record data related to eye-health. The processor is configured to analyze the recorded data, detect a likelihood of eyestrain based on the analysis, and generate an alert to perform at least one action in response to the detection and based on the analysis.

20 Claims, 4 Drawing Sheets

(56) References Cited

OTHER PUBLICATIONS

Mediafox Marketing S.R.O, "Eye Exercises," http://exercises4eyes.com/, Jul. 19, 2016, 1 page.
gadgets.ndtv.com, "'Blink' App Enables Eye Exams at Home Via Smartphone," http://gadgets.ndtv.com/apps/news/blink-app-enables-eye-exams-at-home-via-smartphone-684772, Apr. 23, 2015, 1 page.
Nichole Baxter, "Eye-Related Apps," http://www.allaboutvision.com/apps/, Jun. 8, 2016, 12 pages.
lifehack.org, "Ditch Computer Eye Strain With These 8 Free Apps," http://www.lifehack.org/articles/lifestyle/ditch-computer-eye-strain-with-these-8-free-apps.html, Sep. 16, 2016, 8 pages.

* cited by examiner

VISUAL HEALTH MAINTENANCE AND IMPROVEMENT

BACKGROUND

As computers have become critical tools in the modern economy, computer-related eyestrain has become a major problem associated with the workplace. For example, a worker who frequently uses a computer may suffer from the effects of eyestrain, thereby leading to potential visual health problems. Studies have shown that eyestrain and other bothersome visual symptoms may occur in as much as 50-90% of computer workers. These problems may range from physical fatigue, decreased productivity and increased numbers of work errors, to symptoms such as eye twitch, red eye and/or long-term effects on visual acuity.

Various studies have shown that performing eye exercises to train eye muscles may reduce the effects of eyestrain. For example, regular eye exercises can help to improve eyesight and prevent eye diseases such as myopia (i.e., near-sightedness). Current eyestrain mitigation techniques generally involve taking regular breaks throughout the course of the workday, or altering a computer display (e.g., altering the brightness of the display).

SUMMARY

Illustrative embodiments of the invention provide techniques for maintaining and improving visual health. While illustrative embodiments are well-suited to maintain and improve visual health, alternative embodiments may be implemented.

For example, in one illustrative embodiment, a system to monitor visual health includes a processor operatively coupled to memory. The system further includes one or more subsystems configured to record data related to eye-health. The processor is configured to analyze the recorded data, detect a likelihood of eyestrain based on the analysis, and generate an alert to perform at least one action in response to the detection and based on at least a portion of the recorded data.

For example, in another illustrative embodiment, a method for monitoring visual health includes recording data related to eye-health. The recorded data is analyzed, and a likelihood of eyestrain is detected based on the analysis. An alert is generated to perform at least one action in response to the detection and based on at least a portion of the recorded data.

The embodiments described herein may further be embodied in a computer program product.

DETAILED DESCRIPTION

In illustrative embodiments, techniques are provided for performing visual training eye exercises. More particularly, illustrative embodiments provide techniques for achieving eye-fitness goals. As will be explained in illustrative embodiments, the illustrative embodiments advantageously improve relieve eyestrain, reduce the risk of eyestrain, and maintain visual health.

Figure 1:
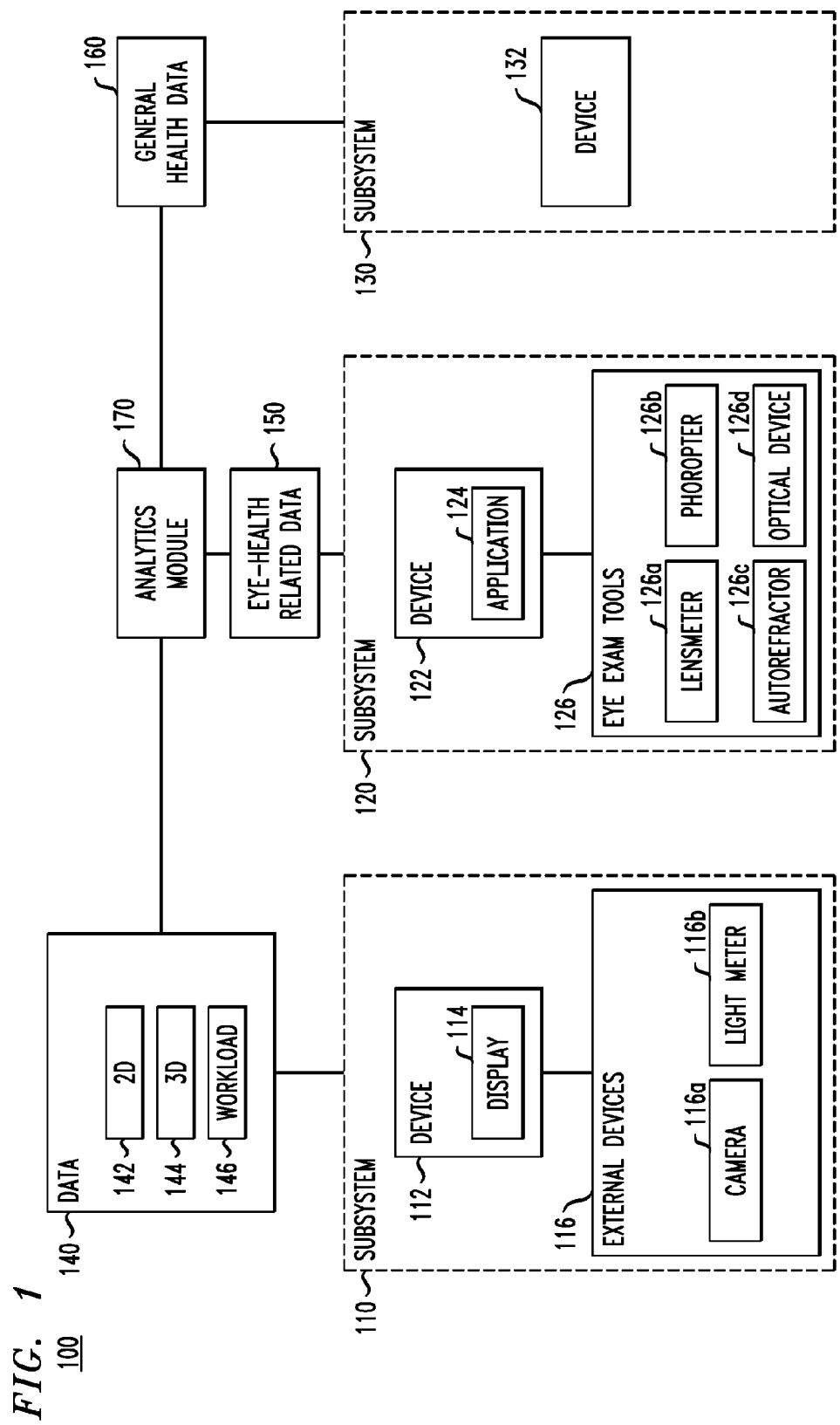
FIG. 1 depicts a block diagram illustrating an overview of a system configured to improve visual health, according to an embodiment of the invention.

With reference to FIG. 1, a block diagram is provided illustrating an overview of an eyestrain detection and mitigation system 100. System 100 may be interpreted as being comprised of three "subsystems," including subsystem 110, subsystem 120 and subsystem 130. Although subsystems 110, 120 and 130 are depicted in FIG. 1 as being individual subsystems of system 100, this depiction is purely exemplary for the ease in description. For example, subsystems 110, 120 and 130 may be alternatively be embodied within a single combination, or as a combination of sub-combinations of subsystems.

As shown, subsystem 110 may comprise device 112, display 114 and external devices 116 operatively coupled to device 112. Although display 114 is shown comprised within device 112, display 114 may be separately connected to device 112. Furthermore, although external device 116 are shown external to device 112, one or more devices of external devices 116 may be comprised within device 112 (i.e., built-into device 112). Accordingly, the arrangement of the components of subsystem 110 depicted in FIG. 1 is not to be considered limiting.

Subsystem 110 may be a computer system configured to record and output data 140 related to eyestrain for a user and analyze the captured data for anti-pattern, outliers, negative behavior, etc. Data 140 may comprise data captured by one or more components of subsystem 110. In one embodiment, data 140 is used to detect a probability or likelihood that a user may be at risk for eyestrain. As shown, data 140 may comprise set of two-dimensional (2D) parameters 142. Set of 2D parameters 142 may comprise one or more parameters related to data associated with subsystem 110. For example, set of 2D parameters 142 may include parameters related to glare by luminance cameras, computer display settings, etc. Data 140 may further comprise set of three-dimensional (3D) parameters 144. Set of 3D parameters 144 may comprise one or more parameters related to the environment of the user. For example, set of 3D parameters 144 may include parameters related to user positioning, mouse scrolling pattern, light level and/or angle, etc. In one embodiment, external devices 116 are configured to obtain data associated with set of 3D parameters 144.

In one embodiment, external devices 116 comprise one or more devices configured to capture 3D parameters 144 for recording by subsystem 110. For example, as shown, external devices 116 may include camera 116a and light meter 116b. Camera 116a may be configured to capture visual data in order to monitor one or more user parameters. The one or more user parameters may include, for example, user positioning parameters, blinking frequency, eye position, etc. Light meter 116b be configured to capture light level and/or angle parameters.

Data 140 may further comprise set of workload pattern data 146. Workload pattern data 146 is associated with a workload pattern of the user and may represent another source of data that may be used to determine eyestrain risk for the user. For instance, a user who is working for an extended period of time on the computer system may be more susceptible to eyestrain. Thus, an analysis of workload pattern data of the user may determine an amount of time that the user has been working (e.g., daily, weekly, etc.). Workload pattern data 146 may be extracted from various sources, including but not limited to an electronic calendar, a travel log, and location information (e.g., location information from GPS tracking applications).

Subsystem 120 is shown comprising device 122 and application ("app") 124. In one embodiment, device 122 is a mobile device. For example, device 122 may be a smartphone, tablet, or any other type of mobile device in accordance with the embodiments described herein. Subsystem 120 may be an eye-health recording system configured to record and output eye-health data 150. In one embodiment, subsystem 120 is configured to periodically record the eye-health data 150. Eye-health data 150 may comprise current eye-health data associated with a user. In one embodiment, eye-health data 150 is recorded via app 124. For example, device 122 is operatively coupled to eye exam tools 126, and app 124 is configured to record data obtained from eye exam tools 140.

Eye exam tools 126 may comprise one or more tools configured to measure eye-health data 150. As shown in this illustrative embodiment, set of eye exam tools 126 may comprise lensmeter 126a to measure the prescription strength of a user's existing glasses, phoropter 126b to measure a user's refractive error and determine an eyeglass prescription, autorefractor 126c to measure a user's level of focusing error and/or at least one optical imaging device 126d to capture high-quality images of the eye (e.g., the fundus). For example, optical device 126d may be configured to perform optical coherence tomography (OCT) to capture retinal images. This imaging performed by optical device 126d may provide information about an eye condition of the user that cannot be determined based solely on the eyesight error information obtained from the other tools. For example, optical device 126d may be used to detect an eye disease, like retinitis pigmentosa, macular degeneration, glaucoma, diabetic retinopathy, ocular infections, etc., as well as provide an accurate evaluation of the stages of the eye disease.

It is to be understood that the eye exam tools described herein and shown in FIG. 1 represent an exemplary collection of eye exam tools, and it is to be appreciated that any eye-health measurement tools may be implemented to measure and gather eye-related health data, in accordance with the embodiments described herein. In addition, although the one or more tools are depicted as individual tools, the one or more tools may be combined into a single tool, or may be a combination of individual tools and combinations of tools.

In another embodiment, the eye-health data 150 is recorded via manual user input. The manual user input may be used to supplement data obtained by eye exam tools 126, or may be used in lieu of data obtained by eye exam tools 126. In one embodiment, eye-health related data 150 comprises a list of eye health parameter values and disease information. For example, eye-health data 150 may be recorded in text format.

Subsystem 130 is shown comprising device 132. In one embodiment, device 132 is a wearable device. For example, device 132 may be a wireless-enabled fitness tracker (e.g., Fitbit®). However, device 132 may be any device that may be configured to operate in accordance with the embodiments described herein, such as a smartphone, a tablet device, a laptop, etc. Device 132 is configured to record and output general health data 160 associated with a user. General health data 160 may comprise additional eyestrain related general health data, such as data related to strain or fatigue. For example, general health data 160 may include sleep pattern data, headache pattern data, heart rate data, blood pressure data, sinus condition data, etc.

The data recorded by one or more of subsystems 110, 120 and 130 (i.e., data 140, eye-health data 150 and general health data 160) may be output to analytics module 170 for analysis. In this illustrative embodiment, analytics module 170 is shown outside of subsystem 110, subsystem 120 and subsystem 130. However, analytics module 170 can be implemented in one or more of the subsystems 110, 120 and 130, in a standalone device, or some combination thereof.

Eye-health related data 150 and general health data 160 may be used by analytics module 170 to measure and monitor eye-fitness goals personalized for a particular user based on the eye condition of the user. Eye-health related data 150 and general health data 160 may further be used by analytics module 170 to recommend or suggest actions, such as eye exercises, based on the eye condition of the user. For example, the health data recorded by subsystem 120 and subsystem 130 may be combined with set of 2D parameters 142 and set of 3D parameters 144 to measure eye-strain probability and determine appropriate eye exercises for the user. In one embodiment, the suggested actions are determined based on eye-health related data 150 and general health data 160. The suggested actions may include, for example, blinking, gazing at a distant object, palming, swinging, sunning, central fixation, shifting, etc. The suggested actions, or eye exercises, are designed to be easy, while effectively reducing the risk of eyestrain. Otherwise high level and specialized visual training exercises may be suggested based on eyestrain and overall user eye health.

If a user is performing the suggested actions, the probability of eyestrain should decrease and can therefore be monitored. In one embodiment, system 100 is configured to monitor the performance of the suggested actions. For example, system 100 may be configured to monitor a degree to which a user is performing the suggested actions.

Analytics module 170 may be further configured to dynamically adjust an eye-fitness goal for the user based on an updated visual performance. For example, analytics module may recalculate the eye-fitness goal based on eye-health related data 150 and general health data 160. In one embodiment, analytics module 170 is configured to prompt or alert the user to take one or more appropriate eye exercises in accordance with a current eye-fitness goal of the user. For example, analytics module 170 may prompt or alert the user, such as with a beeping sound, to perform an eye exercise, when necessary, in accordance with the eye-fitness goal.

In one embodiment, a machine learning algorithm may be implemented to incorporate a feedback aspect within system 100. The machine learning algorithm may determine one or more threshold levels that indicate the onset of eye-strain. Over time, the system monitors the relevant parameters to determine if the recommended exercises have changed the relevant parameters and hence, have improved or degraded the eye-condition. This can be determined by comparing the recorded parameters against their respective thresholds. This process may repeated until the eye-condition is showing signs of improvement (i.e., the parameters go back to the normal range) or if external intervention is determined to be required (e.g. suggest meeting a general practitioner).

The machine learning algorithm may be used to adjust the threshold levels associated with each parameter over time. This training allows the machine learning algorithm to automatically customize and personalize the thresholds for eyestrain detection based on user observation over time. For example, the eye blink rate of the user may be dynamically observed in order to determine an appropriate threshold eye blink rate that would suggest eyestrain for the particular user. As another example, the distance of the eyes of the user from display 114 may be dynamically observed in order to determine an appropriate threshold eye distance that would suggest eyestrain for the particular user. Various machine learning algorithms in accordance with the embodiments herein are known in the art, and a further discussion of specific algorithms will not be provided herein.

As mentioned, set of 2D parameters 142 and set of 3D parameters 144 are used by system 100 to detect a probability or likelihood that a user is exposed to an eyestrain risk. For example, one 3D parameter may be a distance of the eyes of the user from display 114. This parameter may be dynamically obtained and analyzed to detect a possibility of eyestrain. As an illustrative example, if the eyes of the user are normally at a position of 1.5 feet from display 114, but over time the eyes of the user are at a position of 1 foot from display 114, this could indicate behavior associated with eyestrain or developing eyestrain. Thus, one or more of the 3D parameters may pertain to user positioning, or ergonomic-related eyestrain. Accordingly, one or more of the 3D parameters may be dynamically obtained and analyzed while a user is using device 112.

In one embodiment, the alert generation module is configured to generate an alert in response to detection of potential eyestrain based on set of 2D parameters 142 and set of 3D parameters 144. The alert may make suggestions regarding a type of eye exercise to be performed, when the eye exercise should be performed, etc. The combination of set of 2D parameters 142 and set of 3D parameters 144 may be further used to calculate the timing of when to perform the exercises, as well as the length of each exercise to be performed.

For example, system 100 may be further configured to generate one or more alert messages by comparing each parameter to a threshold level. For example, a threshold level may be associated with eye distance from the monitor. If the threshold level is set for 1 foot, then system 100 may be configured to generate an alert if the eye distance falls below 1 foot. Another example of a parameter may be eye blinking rate, which may be a symptom of eye tiredness or eyestrain. The eye blinking rate of the user may be compared to a threshold eye blinking rate as another factor in the detection of eyestrain.

As another example, system 100 may be configured to determine a position of the user relative to device 112 and/or display 114 (e.g., user posture). If system 100 determines a user positioning error, system 100 may generate an alert to warn the user that eyestrain may occur within a certain period of time if the user positioning error is left uncorrected (e.g., system 100 may generate an alert if there is a risk of eyestrain within the next two hours if the user positioning error is not corrected). The alert may include a suggestion to correct the user positioning error, such as suggesting that the user correct his or her posture. If the user positioning error cannot be corrected, system 100 may make other suggestions to reduce the effect of the user positioning error on eye health, such as a suggestion take a break and/or perform an exercise every two hours.

As another example, system 100 may be configured to determine a light level and/or display settings. If system 100 determines a light level error, system 100 may generate an alert to warn the user that eyestrain may occur within a certain period of time if the light level error is left uncorrected (e.g., system 100 may generate an alert if there is a risk of eyestrain within the next hour if the light level error is not corrected). This alert may include a suggestion to correct the light level error, such as a suggestion that the user change the light level of the environment. If the light level error cannot be corrected, system 100 may make other suggestions to reduce the effect of the light level error on eye health, such as resting the eyes after every hour. If system 100 detects a display settings error, system 100 may generate an alert to warn the user that eyestrain may occur within a certain period of time if the display setting error is left uncorrected (e.g., system 100 may generate an alert if there is a risk of eyestrain within the next half hour if the display setting error is not corrected). This alert may include a suggestion to correct the display setting error. If the display settings are left unchanged, system 100 may make other suggestions to reduce the effect of the display setting error on eye health, such as resting the eyes every half hour. Additionally, system 100 may be configured to detect glare, which is associated with a risk of eyestrain. If system 100 detects glare, system 100 may generate an alert to change the display settings of display 114 and/or the light level of the environment to reduce the glare.

As another example, system 100 may be configured to determine a mouse scrolling pattern associated with the user based on set of 3D parameters 144. If system 100 determines that the mouse scrolling pattern suggests ongoing or imminent eyestrain, system 100 may generate an alert to warn the user the ongoing or imminent eyestrain. This alert may include a suggestion to take immediate measures, which may require longer eye rest and/or eye refreshing exercises.

To illustrate the interplay between set of 2D parameters 142 and set of 3D parameters 144 described herein, consider the following use-case. An employee is working on a laptop, which may be an example of device 112 having built-in display 114. Based on the mouse scrolling pattern, an inference could be drawn by conventional systems that the user is confused or sleep deprived. However, a system that bases its decision solely by examining the mouse scrolling pattern may provide suggestions that are not specifically geared toward the current health of the user. In contrast to such conventional systems, the mouse scrolling pattern may be analyzed by system 100 in conjunction with set of 2D parameters 142 associated with the laptop (e.g., display settings) to provide a more targeted remedial action (e.g., take a short break immediately), as well to provide suggestions regarding changes that may be made to one or more parameters of set of 2D parameters 142 to reduce the risk of eyestrain. For example, system 100 could suggest changing the display settings of the laptop to appropriately match the environmental conditions in which the user is located. Accordingly, by examining both set of 2D parameters 142 and set of 3D parameters 144, a more accurate conclusion regarding the eye condition of a user may be drawn, which allows for better detection and correction of eye health problems. Accordingly, system 100 is configured to detect eyestrain in real-time or near-real-time by analyzing one or more parameters.

In one embodiment, system 100 may be configured to generate an alert to perform an appropriate visual acuity improvement exercise when device 112 and/or display 114 is in an "inactive" or "idle" state. The alert may be any type of alert or combination of types of alerts. For example, the alert may include one or more of an audible alert, a visual alert, a vibrational alert, etc.

The system of FIG. 1 is configured to achieve personalized eye-fitness goal in an efficient manner. As discussed, the system is configured to capture personalized health data (e.g., current eye-health data and any additional eyestrain related general health data), as well as 2D parameter data, 3D parameter data and current workload data, in order to determine an efficient eye-fitness course of action. The system may be configured to fit an appropriate visual acuity improvement exercise schedule, thereby lessening the negative impact of performing the eye-fitness exercises with respect to worker productivity. The system of FIG. 1 may prompt or alert the user to perform an action to reduce eyestrain. For example, the system may inform the user to make an adjustment, such as an adjustment to an ideal chair height if the eye position of the user is determined to be causing eyestrain.

Figure 2:
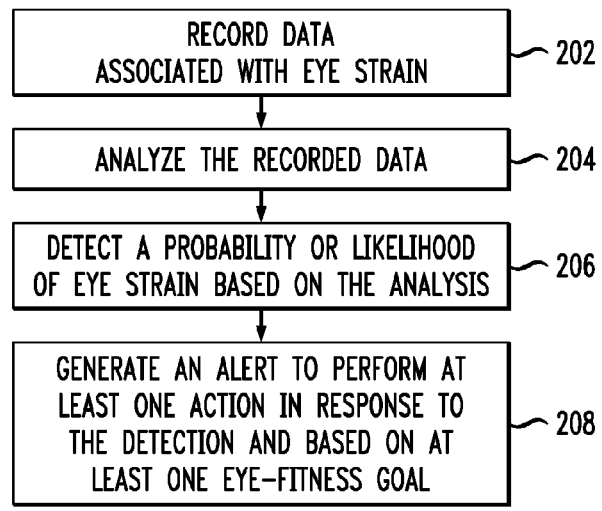
FIG. 2 depicts a flow chart illustrating a process for preventing and treating eye-strain, according to an embodiment of the invention.

With reference to FIG. 2, a flowchart 200 is provided illustrating a process for preventing and/or treating eye strain. At step 202, data related to eye strain is recorded. In one embodiment, the data related to eye-health comprises a set of 2D parameters and a set of 3D parameters. As discussed above in FIG. 1, the set of 2D parameters may comprise one or more parameters related to a computing device and/or display associated with the computing device. For example, the set of 2D parameters may comprise parameters related to glare by luminance cameras, computer display settings, etc. As discussed above in FIG. 1, the set of 3D parameters may comprise one or more parameters related to an environment of the user. For example, the set of 3D parameters may include parameters related to user positioning, mouse scrolling pattern, light level and/or angle, etc. In one embodiment, recording the set of 3D parameters comprises obtaining at least a portion of the set of 3D parameters via one or more external devices. The one or more external devices may comprise a camera, a light meter, etc.

The data related to eye-health may further comprise workload pattern data. As discussed above in FIG. 1, the workload pattern data is associated with a workload pattern of the user and may represent another source of data that may be used to determine eyestrain risk for the user. For instance, a user who is working for an extended period of time on the computer system may be more susceptible to eyestrain. Thus, an analysis of workload pattern data of the user may determine an amount of time that the user has been working (e.g., daily, weekly, etc.). The workload pattern data may be extracted from various sources, such as from an electronic calendar of the user.

At step 204, the recorded data is analyzed and, at step 206, a probability or likelihood of eye strain is detected based on the analysis. At step 208, in response to the detection at step 206, an alert is generated to perform at least one action in response to the detection and based on at least a portion of the recorded data. In one embodiment, recorded data may further comprise current eye-health data and/or general health data associated with the user, and the at least one action may be determined based on the current eye-health data and/or general health data. As discussed in FIG. 1, the current eye-health data may be obtained via one or more eye exam tools and/or may be manually entered by the user.

The at least one action may be determined based on one or more personalized eye-fitness goals associated with the user. The suggested actions may include, for example, blinking, gazing at a distant object, palming, swinging, sunning, central fixation, shifting, etc. Each action, or eye exercise, is designed to be easy, while effectively reducing the risk of eyestrain. Other high level and specialized visual training exercises may be suggested based on eyestrain and overall user eye health. In one embodiment, an alert is generated to perform an appropriate visual acuity improvement exercise when the computing device and/or display is determined to be in an "inactive" or "idle" state. The alert may be any type of alert or combination of types of alerts. For example, the alert may include one or more of an audible alert, a visual alert, a vibrational alert, etc.

Figure 3:
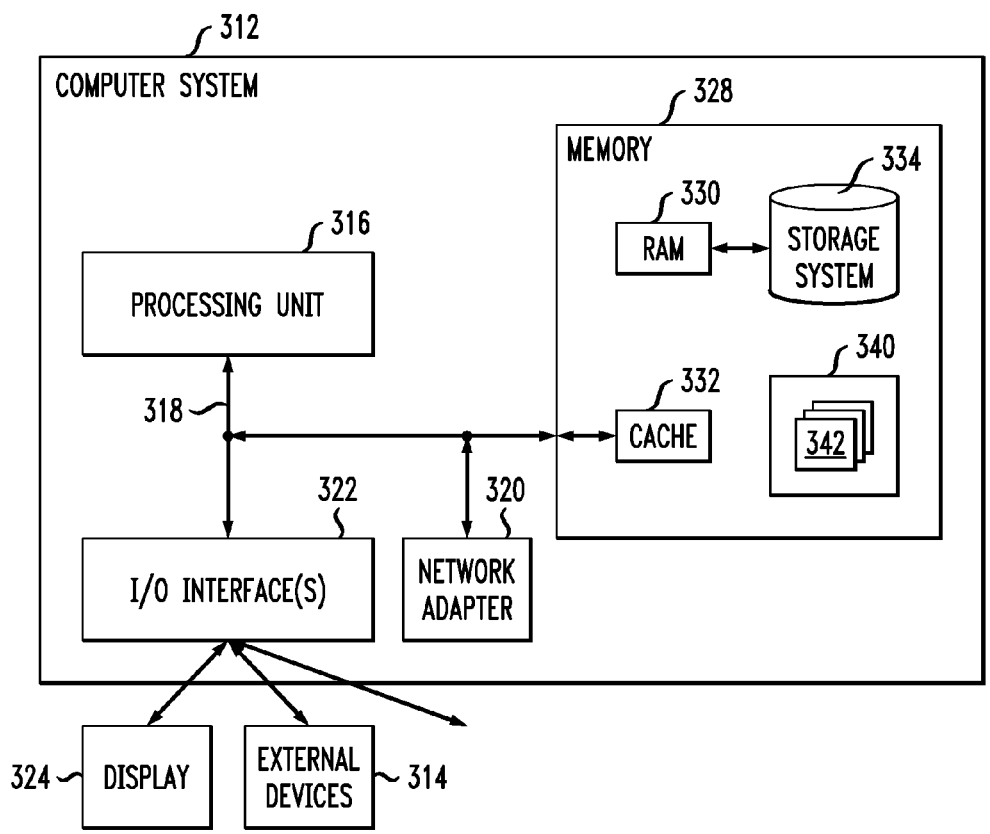
FIG. 3 depicts a computer system in accordance with which one or more components/steps of techniques of the invention may be implemented, according to an embodiment of the invention.

One or more embodiments can make use of software running on a computer or workstation. With reference to FIG. 3, in a computing node 310 there is a system/server 312, which is operational with numerous other general purpose or special purpose computing system environments or configurations. Examples of well-known computing systems, environments, and/or configurations that may be suitable for use with system/server 312 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

System/server 312 may be described in the general context of computer system executable instructions, such as program modules, being executed by a computer system. Generally, program modules may include routines, programs, objects, components, logic, data structures, and so on that perform particular tasks or implement particular abstract data types. System/server 312 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, system/server 312 is shown in the form of a computing device. The components of system/server 312 may include, but are not limited to, one or more processors or processing units 316, system memory 328, and bus 318 that couples various system components including system memory 328 to processor 316.

Bus 318 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

System/server 312 typically includes a variety of computer system readable media. Such media may be any available media that is accessible by system/server 312, and it includes both volatile and non-volatile media, removable and non-removable media.

The system memory 328 can include computer system readable media in the form of volatile memory, such as random access memory (RAM) 330 and/or cache memory 332. System/server 312 may further include other removable/non-removable, volatile/nonvolatile computer system storage media. By way of example only, storage system 334 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 318 by one or more data media interfaces.

As depicted and described herein, memory 328 may include at least one program product having a set (e.g., at least one) of program modules that are configured to carry out the functions of embodiments of the invention. A program/utility 340, having a set (at least one) of program modules 342, may be stored in memory 328 by way of example, and not limitation, as well as an operating system, one or more application programs, other program modules, and program data. Each of the operating system, one or more application programs, other program modules, and program data or some combination thereof, may include an implementation of a networking environment. Program modules 342 generally carry out the functions and/or methodologies of embodiments of the invention as described herein.

System/server 312 may also communicate with one or more external devices 314 such as a keyboard, a pointing device, an external data storage device (e.g., a USB drive), display 324, one or more devices that enable a user to interact with system/server 312, and/or any devices (e.g., network card, modem, etc.) that enable system/server 312 to communicate with one or more other computing devices. Such communication can occur via I/O interfaces 322. Still yet, system/server 312 can communicate with one or more networks such as a LAN, a general WAN, and/or a public network (e.g., the Internet) via network adapter 320. As depicted, network adapter 320 communicates with the other components of system/server 312 via bus 318. It should be understood that although not shown, other hardware and/or software components could be used in conjunction with system/server 312. Examples include, but are not limited to, microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
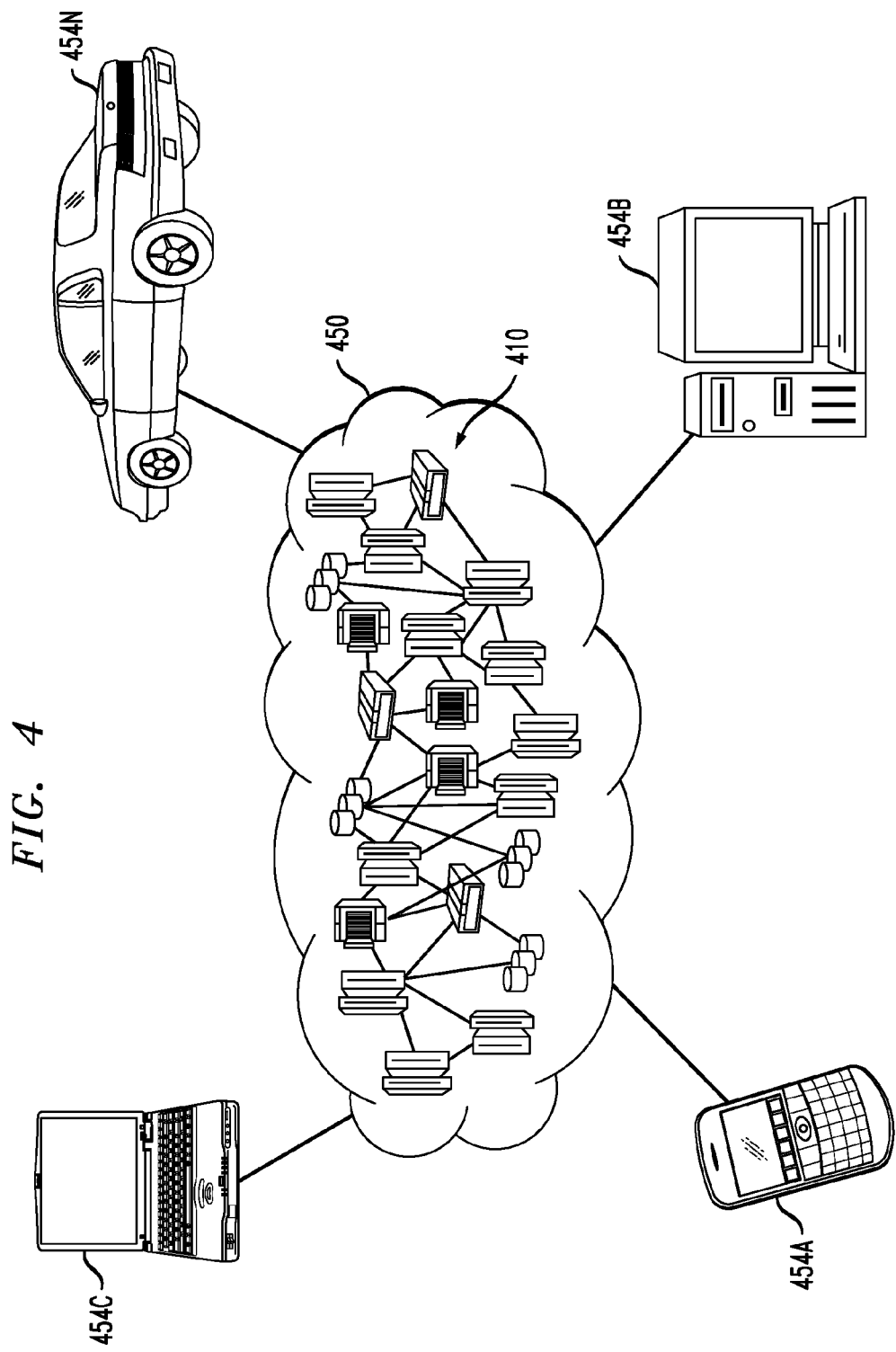
FIG. 4 depicts a cloud computing environment, according to an embodiment of the invention.

Referring now to FIG. 4, illustrative cloud computing environment 450 is depicted. As shown, cloud computing environment 450 includes one or more cloud computing nodes 410 with which local computing devices used by cloud consumers, such as, for example, personal digital assistant (PDA) or cellular telephone 454A, desktop computer 454B, laptop computer 454C, and/or automobile computer system 454N may communicate. Nodes 410 may communicate with one another. They may be grouped (not shown) physically or virtually, in one or more networks, such as Private, Community, Public, or Hybrid clouds as described hereinabove, or a combination thereof. This allows cloud computing environment 450 to offer infrastructure, platforms and/or software as services for which a cloud consumer does not need to maintain resources on a local computing device. It is understood that the types of computing devices 454A-N shown in FIG. 4 are intended to be illustrative only and that computing nodes 410 and cloud computing environment 450 can communicate with any type of computerized device over any type of network and/or network addressable connection (e.g., using a web browser).

Figure 5:
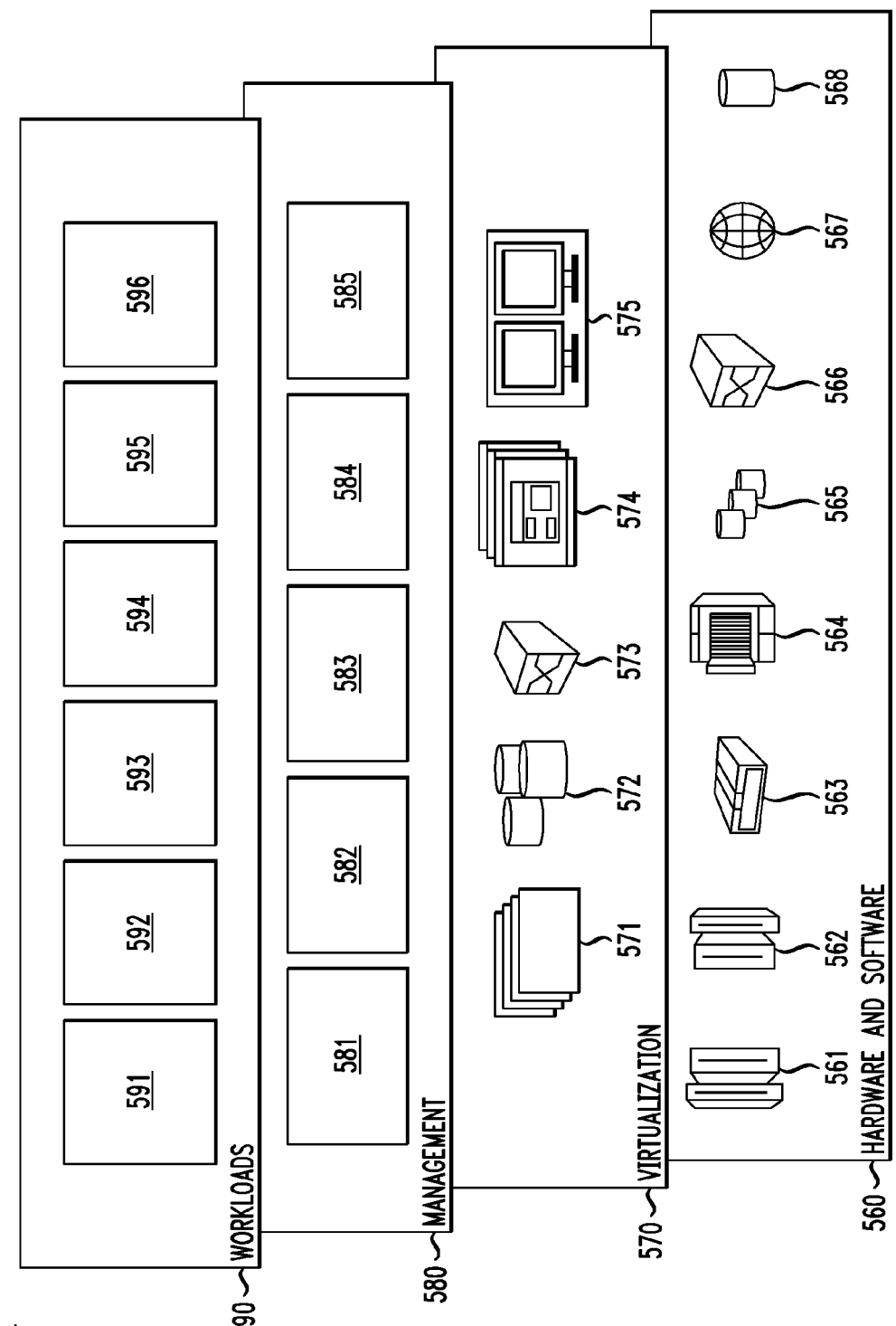
FIG. 5 depicts abstraction model layers, according to an embodiment of the present invention.

Referring now to FIG. 5, a set of functional abstraction layers provided by cloud computing environment 450 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 560 includes hardware and software components. Examples of hardware components include: mainframes 561; RISC (Reduced Instruction Set Computer) architecture based servers 562; servers 563; blade servers 564; storage devices 565; and networks and networking components 566. In some embodiments, software components include network application server software 567 and database software 568.

Virtualization layer 570 provides an abstraction layer from which the following examples of virtual entities may be provided: virtual servers 571; virtual storage 572; virtual networks 573, including virtual private networks; virtual applications and operating systems 574; and virtual clients 575.

In one example, management layer 580 may provide the functions described below. Resource provisioning 581 provides dynamic procurement of computing resources and other resources that are utilized to perform tasks within the cloud computing environment. Metering and Pricing 582 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 583 provides access to the cloud computing environment for consumers and system administrators. Service level management 584 provides cloud computing resource allocation and management such that required service levels are met. Service Level Agreement (SLA) planning and fulfillment 585 provide pre-arrangement for, and procurement of, cloud computing resources for which a future requirement is anticipated in accordance with an SLA.

Workloads layer 590 provides examples of functionality for which the cloud computing environment may be utilized. Examples of workloads and functions which may be provided from this layer include: mapping and navigation 591; software development and lifecycle management 592; virtual classroom education delivery 593; data analytics processing 594; transaction processing 595; and visual health processing 596, which may perform various functions described above.

The embodiments described herein advantageously improve visual health over conventional systems and techniques. For example, the embodiments described herein advantageously consider both two-dimensional parameters (e.g., glare by luminance cameras and computer display settings) and three-dimensional parameters (e.g., a positioning of a user, mouse scrolling patterns and light/level angle in a workplace) to measure eyestrain probability. The embodiments described herein advantageously consider the existing medical condition of the eye(s) and other eyestrain-related general health data (e.g., sleep patterns, headache patterns, blood pressure and sinus conditions) when choosing a course of action in mitigating eyestrain. For example, eyestrain mitigation measures may be different for a person with a history of ocular migraine as compared to a person without a history of ocular migraine. Taking such personalized health data into consideration allows for a more customized eyestrain mitigation protocol and, advantageously, provides advice and suggestions regarding appropriate eye exercises to maintain or improve eyestrain condition and overall visual health. Thus, the embodiments described herein can allow for the continuous adjustment of an eye-fitness goal for a user using information associated with a current eyestrain level and information associated with overall eye health and, based on the eye-fitness goal, advise appropriate eye-exercises to maintain and/or improve an eyestrain condition and overall visual health of the user. Accordingly, the embodiments described herein advantageously synchronize eyestrain mitigation with any overall eye-fitness goal of the user.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although illustrative embodiments have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A system comprising:
  at least one processor operatively coupled to at least one memory; and
  one or more subsystems associated with the at least one processor;
  wherein the one or more subsystems comprise a computing device operatively coupled to at least one external device; and
  wherein the at least one processor is configured to:
    record data, the data comprising:
      one or more parameters relating to data associated with settings of the computing device;
      one or more parameters relating to an environment of a user operating the computing device obtained via the at least one external device while the user is operating the computing device; and
      health data related to the user, wherein the health data comprises current eye-health data of the user and general health data of the user;
    analyze the recorded data;
    detect a likelihood of eyestrain based on the analysis; and
    generate an alert to perform at least one action in response to the detection and based on the analysis.

2. The system of claim 1, wherein the recorded data further comprises workload pattern data.

3. The system of claim 1, wherein the at least one external device comprises a camera, and wherein at least a portion of the set of 3D parameters is obtained via the camera while the user is operating the computing device.

4. The system of claim 1, wherein the at least one external device comprises a light meter, and wherein at least a portion of the set of 3D parameters is obtained via the light meter while the user is operating the computing device.

5. The system of claim 1, wherein the at least one alert is generated by comparing at least a portion of the recorded data to one or more respective thresholds.

6. The system of claim 5, wherein the at least one processor is further configured to implement a machine learning algorithm to dynamically modify the one or more thresholds.

7. The system of claim 1, further comprising a set of eye exam tools configured to obtain at least a portion of the recorded health data.

8. The system of claim 1, wherein at least a portion of the recorded health data is manually provided.

9. The system of claim 1, wherein the at least one processor is further configured to dynamically calculate an eye-fitness goal based at least on a portion of the recorded data, and wherein the at least one action is determined based on the eye-fitness goal.

10. The system of claim 1, wherein the at least one processor is further configured to generate an alert to perform one or more visual acuity improvement exercises for performance during idle times associated with the user.

11. A method comprising:
recording data, the data comprising:
one or more parameters relating to data associated with settings of a computing device comprised within one or more subsystems;
one or more parameters relating to an environment of a user operating the computing device obtained via at least one external device operatively coupled to the computing device while the user is operating the computing device; and
health data related to the user, wherein the health data comprises current eye-health data of the user and general health data of the user;
analyzing the recorded data;
detecting a likelihood of eyestrain based on the analysis; and
generating an alert to perform at least one action in response to the detection and based on the analysis;
wherein the steps of the method are implemented by at least one processing device comprising a processor operatively coupled to a memory.

12. The method of claim 11, wherein the recorded data further comprises workload pattern data.

13. The method of claim 11, wherein generating the at least one alert comprises comparing at least a portion of the recorded data to one or more respective thresholds.

14. The method of claim 13, further comprising implementing a machine learning algorithm to dynamically modify the one or more thresholds.

15. The method of claim 11, further comprising dynamically calculating an eye-fitness goal based at least on a portion of the recorded data, wherein the at least one action is determined based on the eye-fitness goal.

16. The method claim 11, further comprising generating an alert to perform one or more visual acuity improvement exercises for performance during idle times associated with the user.

17. An article of manufacture comprising a processor readable storage medium for storing computer readable program code which, when executed, causes a processor to:
record data, the data comprising:
one or more parameters relating to data associated with settings of a computing device comprised within one or more subsystems;
one or more parameters relating to an environment of a user operating the computing device obtained via at least one external device operatively coupled to the computing device while the user is operating the computing device; and
health data related to the user, wherein the health data comprises current eye-health data of the user and general health data of the user;
analyze the recorded data;
detect a likelihood of eyestrain based on the analysis; and
generate an alert to perform at least one action in response to the detection and based on the analysis.

18. The method of claim 11, wherein the at least one external device comprises at least one of a camera and a light meter, and wherein at least a portion of the set of 3D parameters is obtained via the at least one the camera and the light meter while the user is operating the computing device.

19. The method of claim 11, further comprising configuring a set of eye exam tools to obtain at least a portion of the recorded health data.

20. The method of claim 11, wherein at least a portion of the recorded health data is manually provided.

* * * * *